United States Patent [19]

Jagger et al.

[11] Patent Number: 4,950,249
[45] Date of Patent: Aug. 21, 1990

[54] HYPODERMIC NEEDLE WITH RECLOSABLE SAFETY CAP

[75] Inventors: Janine C. Jagger; Richard D. Pearson, both of Charlottesville, Va.

[73] Assignee: University of Virginia Alumni Patents Foundation, Charlottesville, Va.

[21] Appl. No.: 364,523

[22] Filed: Jun. 9, 1989

Related U.S. Application Data

[63] Continuation of Ser. No. 158,855, Feb. 22, 1988, abandoned.

[51] Int. Cl.⁵ ............................................. A61M 5/32
[52] U.S. Cl. .................................... 604/192; 604/263
[58] Field of Search ............... 604/102, 110, 192, 197, 604/263, 106–109; 128/17, 345; 206/364–366, 370, 380, 371, 601, 604, 607, 458, 459, 602, 467, 469, 470

[56] References Cited

U.S. PATENT DOCUMENTS

| | | | |
|---|---|---|---|
| 4,106,621 | 8/1978 | Sorenson | 206/365 |
| 4,170,993 | 10/1979 | Alvarez | . |
| 4,627,843 | 12/1986 | Raines | 604/192 |
| 4,669,259 | 5/1987 | Landis | 604/192 |
| 4,747,836 | 5/1988 | Luther | 604/198 |
| 4,820,277 | 4/1989 | Norelli | 604/192 |

FOREIGN PATENT DOCUMENTS

| 37519 | 5/1927 | Denmark | 604/106 |
|---|---|---|---|
| 510677 | 12/1920 | France | 604/106 |

Primary Examiner—Randall L. Green
Assistant Examiner—K. M. Reichle
Attorney, Agent, or Firm—James Creighton Wray

[57] ABSTRACT

A hypodermic needle apparatus has a safety cap which is axially split into two halves. The two halves are pivotally connected to a needle hub for movement outwardly in opposite directions by sliding ring which moves over a portion of the needle hub. A method of unsheathing and resheathing a needle is also disclosed.

5 Claims, 2 Drawing Sheets

HYPODERMIC NEEDLE WITH RECLOSABLE SAFETY CAP

This is a continuation of application Ser. No. 158,858, filed Feb. 22, 1988, now abandoned.

BACKGROUND OF THE INVENTION

Accidental needlestick injuries are extremely common in the health care industry due to the conventional ways in which health care workers are required to handle hypodermic needles. Needle-stick injuries can result in the transmission of hepatitis B, non-A, non-B hepatitis and potentially HIV, the virus causing Acquired Immunodeficiency Syndrome.

Accidental needlestick injuries can occur when physicians, nurses or other hospital workers accidentally stick themselves with hypodermic needles after they have been used on patients. Used, exposed and contaminated needles left on work surfaces, in beds, thrown in nonrigid trash receptacles, or even during transport of a proper receptacle, pose a significant health hazard to hospital personnel.

The currently used hypodermic needles provide no means for safely resheathing needles after use and consequently, used hypodermic needles are the most common cause of accidental needlestick injuries in hospitals.

U. S. Pat. No. 4,627,843 protects a needle with a cover which has a longitudinal opening. However, the cover still requires handling in such a manner that endangers the health care worker.

U. S. Pat. No. 4,629,453 shows a conventional needle cover having a large disk-shaped guard flange which may prevent the tip of the needle from contacting the fingers. However, there is still a requirement that during handling, the fingers have to move in the direction of the needle point at some time.

U. S. Pat. No. 4,345,596 shows a cylindrical device which may be separated into longitudinal halves but the patent does not describe a device which cold protect a needle.

U. S. Pat. No. 4,585,437 simply shows a needle guide having longitudinally divided portions of a cone.

U. S. Pat. No. 4,545,374 shows an example of a device in which longitudinally separable cylindrical halves cover a needle. However, there is still a requirement that during handling the fingers and hands of the health care worker move in proximity to the needle point.

U. S. Pat. No. 4,592,744 shows a device created by the present inventors in an effort to overcome the needlestick problem. While the device solves many of the aforementioned problems, a need still exists for a device which is adaptable for use with a conventional hypodermic needle.

SUMMARY OF THE INVENTION

The present invention solves many of the aforementioned problems by providing an apparatus and method for reclosing a hypodermic needle in such a way that the hands of the health care worker may be used to move a safety cap into a needle covering position without positioning the hands at any time near the tip of the needle. Moreover, the present invention alleviates the need for a health care worker to push a cap in the direction of a needle point in a recovering operation.

The present method and apparatus for resheathing a hypodermic needle eliminates the problem of manually recapping needles. The conventional method and apparatus results in a high risk of needle stick injury. The presently used method and apparatus involves a health care worker holding a needle cap and moving the needle cap over the pointed and contaminated needle until the cap is pushfit over the needle hub.

The present invention involves the hypodermic needle and needle cap. In the current design, the needle/hub portion is fitted with a needle cover that holds to the needle hub by a friction or interference fit. The needle hub attaches to a standard disposable syringe by the same friction fit. The needle cover must be removed to expose the needle for use.

The present invention requires that the needle cover be bonded to the needle hub. To expose the needle for use, an external ring on the needle cover is retracted or screwed downwardly towards the base of the needle hub, allowing the needle cover to separate in two directions into a fixed position perpendicular to the needle. The two halves separate because of the elasticity of the plastic material which has been molded in an open (perpendicular) position. When the two halves are closed, a spring force is created where the plastic material joins the cap to the hub so that upon reopening, the spring force helps pivot the two halves outwardly in opposite directions towards the perpendicular disposition.

A medical procedure is performed with the needle cover fully opened in the perpendicular position After completing the medical procedure, the contaminated needle can then be safely covered by sliding or screwing the external ring toward the distal end of the needle, thereby returning the two halves of the needle cover to a closed position, allowing for the safe disposal of the contaminated needle.

An object of the invention is to provide a hypodermic needle apparatus comprising a needle hub having proximal and distal ends and being permanently or temporarily attachable to a disposable syringe or other device by the proximal end, a needle connected to the needle hub at the distal end thereof, a safety cap axially split into two halves and being pivotally connected to the needle hub, and means for moving the two halves between open and closed positions.

In the open position the two halves pivot about 90 degrees outwardly.

Preferably, the moving means further provides means for holding the two halves in the closed position, and the moving means comprise camming means.

Preferably, the camming means comprises a ring slideably supported on the hub and being vertically movable between lower and upper positions and coacting with exterior surfaces of the two halves to impart pivotally, upwardly movement in the two halves to close the two halves around the needle.

The portion of the hub over which the ring slides may be exteriorly threaded and the ring may be interiorly threaded for engagement with the hub. A lower portion of the safety cap may be exteriorly threaded to engage the ring.

Another object of the invention is to provide a method of unsheathing and resheathing a hypodermic needle comprising, splitting a needle cap longitudinally to form two halves, wherein each half is pivotally connected to a needle hub supporting a needle, moving a camming device in a direction opposite a point of the needle, wherein the camming device allows pivotally outwardly movement of the two halves in opposite directions, moving the camming device in a reverse direction thereby imparting pivotally inwardly movement of the two halves until one half abuts the other.

Preferably, the moving steps comprise rotating a threaded ring which threadedly engages the needle hub.

Another object is to provide a hypodermic needle apparatus comprising a needle having a distal pointed end, a needle hub having a proximal end connectable by pushfit or other means to a syringe or other device and having an opposite distal end connected by pushfit to a proximal end of the needle, a ring slideably mounted on and movable over a portion of the needle hub by threaded engagement therewith, a needle cap axially split into two halves and being pivotally connected to the distal end of the needle hub and being closeable around the needle by sliding the ring.

DETAILED DESCRIPTION OF THE DRAWINGS

Figure 1:
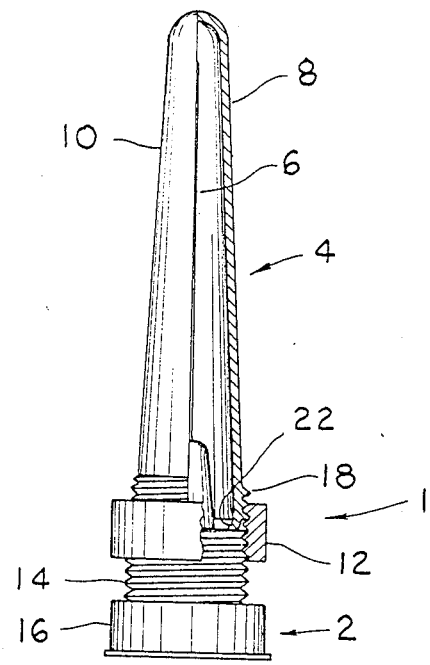
FIG. 1 is a side elevation view, partly in section, and partly in perspective, of a preferred embodiment of the invention.
Figure 2:
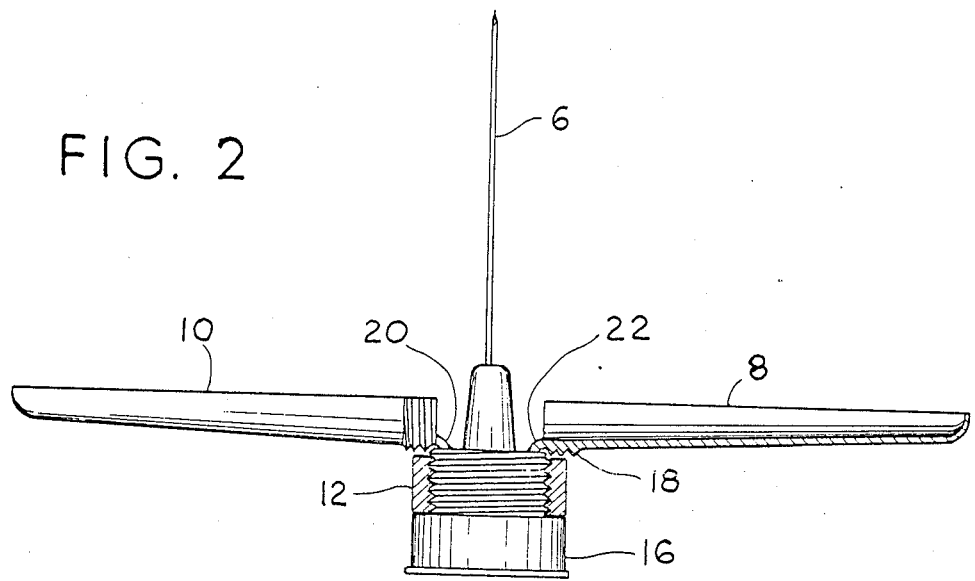
FIG. 2 shows the view of FIG. 1 but with the needle cap in an open position.

Referring to FIGS. 1 and 2, the needle apparatus of the present invention is referred to generally by the numeral 1. The apparatus includes a needle hub 2 and a safety cap 4 which envelopes a pointed needle 6.

The needle 6 is pointed at its distal end and is connected to a distal end of the needle hub at a proximal end of the needle. The drawing shows a conventional connection device between the needle and the hub and is intended to depict a standard hypodermic needle. The needle itself and the connection device are known. Connection of the needle to the hub may be by any conventional means such as a pushfit. Alternatively, the connection device of the needle may be integrally formed with the needle hub. It is within the purview of the skilled practitioner to select the most desirable means of connecting the needle to the needle hub.

The needle cap 4 is split longitudinally into two halves 8, 10 which, in the closed position abut each other as depicted in FIG. 1. In the closed position, the needle 6 is completely enveloped by the cap.

A ring 12 is used to hold the two halves 8, 10 in the closed position, as shown in FIG. 1. The ring 12 is threadedly mounted on a threaded portion 14 of the hub which extends upwardly from a base 16 which is used to attach the apparatus to a conventional syringe or other device and which is held on by a interference fit, fusion welding or permanent bond.

A lower portion of both halves 8, 10 is likewise threaded at the same pitch as the threaded portion 14 of the hub so that, in the preferred embodiment, the ring 12 can firmly hold the two halves in a closed position.

To open the two halves, the ring 12 is rotated in a direction which causes the ring to move axially downwardly along the threaded portion 14.

When the ring reaches the position shown in FIG. 2, the previously described spring force generated by the plastic material which was molded to connect the two halves to the hub at 20, 22, causes the two halves 8, 10 to naturally spring outwardly into the perpendicular position shown in FIG. 2. Reference numerals 20, 22 refer to tabs which link the two halves 8, 10 to the hub at a distal end of the hub. The tabs allow for pivotal movement of the two halves 8, 10 from a full vertical position to a perpendicular position.

To reclose the cap over the needle 6, a health care worker can simply rotate the ring in the opposite direction and an upper end face of the ring will cam outer surfaces of the two halves to impart pivotal movement back to the vertical disposition. Alternatively, the health care worker may first push upwardly with his or her fingers on the outer surfaces of the two halves 8, 10, as shown in FIG. 2, until a full vertical disposition of the two halves is achieved. While holding the two halves in the vertical disposition over the needle, which at this point is fully and safely enveloped by the two halves, the ring 12 can then be rotated to lock the two halves in the closed position.

The invention has many advantages over known types of needle caps in that at no point during the closing procedures does the health care worker have to move his or her hand or fingers in the direction of the needle point. In other words, from the view of FIG. 2, the needle 6 is pointed in the upward direction. Conventional procedures would require the health care worker to hold a needle cap and slide the needle cap over the pointed needle by moving his or her fingers in a downward direction towards the needle point. The present invention removes this hazard because at no time is the health care worker required to move in the direction of the point.

Figure 3:
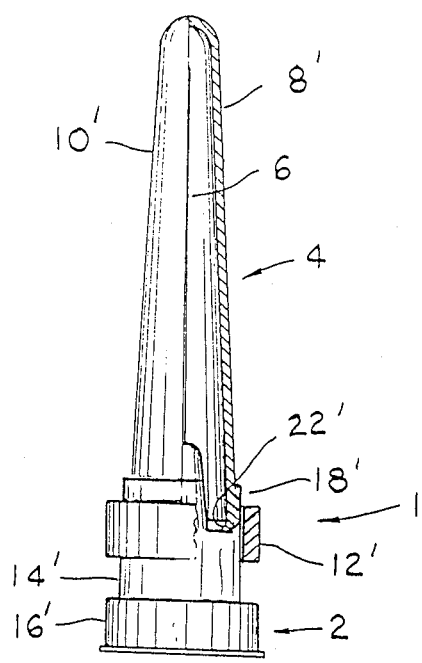
FIGS. 3 and 4 show an alternate sliding embodiment for use with needle assemblies which are screwed on a syringe.
Figure 4:
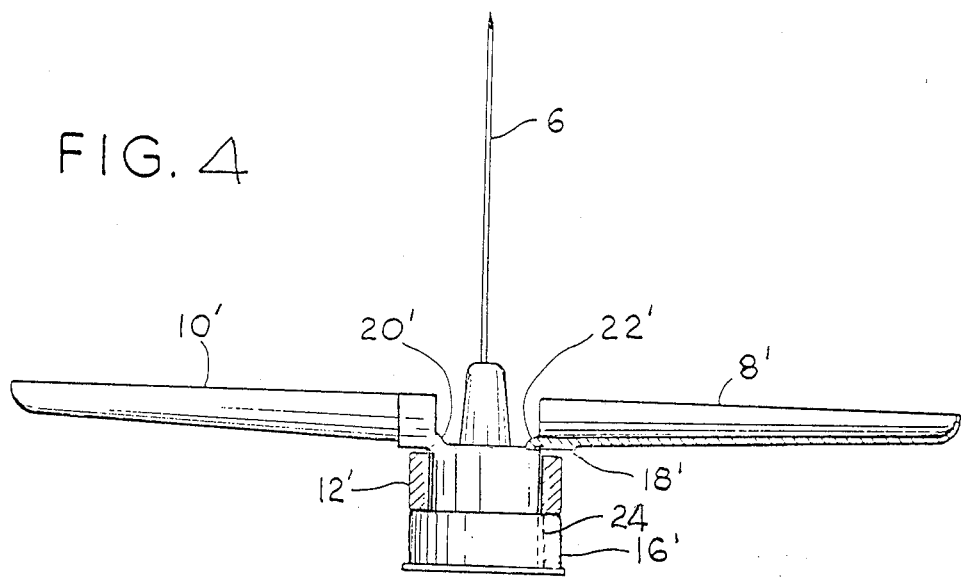

The embodiment shown in FIGS. 3 and 4 is intended for use when the needle base 16' is joined to a syringe by threads 24.

A ring 12' is used to hold the two halves 8', 10' in the closed position, as shown in FIG. 3. The ring 12' is slidably mounted on a portion 14' of the hub which extends upwardly from a base 16' which is used to attach the apparatus to a conventional syringe or other device by screw threads.

A lower portion of both halves 8', 10' is likewise with the same diameter as 14' of the hub so that the ring 12' can firmly hold the two halves in a closed position. To open the two halves, the ring 12 is slid axially downwardly along 14. When the ring reaches the position shown in FIG. 4, the previously described spring force generated by the plastic material which was molded to connect the two halves to the hub at 20', 22', causes the two halves 8', 10' to naturally spring outwardly into the perpendicular position shown in FIG. 4. Reference numerals 20', 22' refer to tabs which link the two halves 8', 10' to the hub at a distal end of the hub. The tabs allow for pivotal movement of the two halves 8', 10' from a full vertical position to a perpendicular position.

To reclose the cap over the needle 6, a health care worker simply slides the ring in the opposite direction and an upper end face of the ring will cam outer surfaces of the two halves to impart pivotal movement back to the vertical disposition. Alternatively, the health care worker may first push upwardly with his or her fingers on the outer surfaces of the two halves 8', 10', until a full vertical disposition of the two halves is achieved. While holding the two halves in the vertical disposition over the needle, which at this point is fully and safely enveloped by the two halves, the ring 12, can then be slid to lock the two halves in the closed position.

While the invention has been described with reference to specific embodiments, modifications and variations of the invention may be constructed without departing from the scope of the invention. The scope of the invention is defined in the following claims.

We claim:

1. A hypodermic needle apparatus comprising:

a needle having a distal end and a proximal end, a needle hub having proximal and distal ends connected to a syringe or other device at its proximal end and connected to the proximal end of the needle at its distal end, a needle cap axially split into two halves along its length and having proximal and distal ends, the length of the halves being at least that of the needle so as to enclose the needle when the distal ends of the two halves are positioned adjacent each other, the closed position, and each half is pivotally connected at its proximal end by tabs to the needle hub, and a ring slidably supported on the hub and being vertically movable between upper and lower positions, wherein in the lower position the ring is below the pivotal connection of the two halves, and in the upper position the distal portion of the ring is slightly above the pivotal connection of the two halves and coacts with the exterior surfaces of the two halves to cause pivotally upward movement of the two halves to close the two halves around the needle when the ring is moved from its lower position to its upper position, wherein the tabs are made of an elastic material which are formed perpendicular with respect to the needle hub, so that the distal ends of the two halves are biased to a position spaced from each other and the halves are biased to extend perpendicular with respect to the needle hub, the open position, such that when the ring is moved from its lower position to its upper position, placing the two halves in its closed position, a spring force is created in the tabs due to the bending of the tabs upwards from their perpendicular position, and such that when the ring is moved from its upper position to its lower position, the spring force created in the tabs is released, causing an outward movement of the two halves to the open position.

2. The apparatus of claim 1 wherein the portion of the hub over which the ring slides is exteriorly threaded and the ring is interiorly threaded for engagement with the hub.

3. The apparatus of claim 4, wherein the proximal end of the needle cap is exteriorly threaded to engage the ring.

4. A method of using a hypodermic needle assembly of claim 1, comprising the following steps:

moving said ring to its lower position, thereby releasing the spring force created in the tabs causing an outward movement of the two halves to the open position and moving said ring back to its upper position, thereby causing pivotally upward movement of the two halves in the closed position, thereby resheathing the needle and recreating the spring force in the tabs.

5. A hypodermic needle apparatus comprising:

a needle having a distal end and a proximal end, a needle hub having proximal and distal ends connectable to a syringe or other device at its proximal end and connected to the proximal end of the needle at its distal end, wherein the distal end of the needle hub is further provided with exterior threads, a needle cap axially split into two halves along its length and having proximal and distal ends, the length of the halves being at least that of the needle so as to enclose the needle when the distal ends of the two halves are positioned adjacent each other, the closed position, and each half is pivotally connected at its proximal end by tabs to the needle hub wherein the proximal end of the needle cap is provided with exterior threads which form an extension of the exterior threads on the distal end of the needle hub, and a ring with interior threads which is threadedly mounted on the exterior threads of the needle hub and the needle cap and is movable between lower and upper positions, wherein in the lower position the ring is below the pivotal connection of the two halves, and wherein in the upper position the distal portion of the ring is slightly above the pivotal connection of the two halves and coacts with the exterior surfaces of the two halves to cause pivotally upward movement of the two halves to close the two halves around the needle when the ring is moved from its lower position to its upper position, and wherein the tabs are made of an elastic material which are formed perpendicular with respect to the needle hub, so that the distal ends of the two halves are biased in a position spaced from each other and the halves are biased to extend perpendicular with respect to the needle hub, the open position, such that when the ring is moved from its lower position to its upper position, placing the two halves in its closed position, a spring force is created in the tabs due to the bending of the tabs upwards from their perpendicular position, and such that when the ring is moved from its upper position to its lower position, the spring force created in the tab is released, causing an outward movement of the two halves to the open position.

* * * * *